United States Patent [19]
Jassim et al.

[11] Patent Number: 5,840,308
[45] Date of Patent: Nov. 24, 1998

[54] ANTIVIRAL OR ANTIFUNGAL COMPOSITION COMPRISING AN EXTRACT OF POMEGRANATE RIND OR OTHER PLANTS AND METHOD OF USE

[75] Inventors: Sabah Abdel Amir Jassim, Nottingham; Stephen Paul Denyer, Lewes; Gordon Sydney Anderson Birnie Stewart, Loughborough, all of United Kingdom

[73] Assignee: Merck Patent GmbH, Darmstadt, Germany

[21] Appl. No.: 632,455

[22] PCT Filed: Feb. 16, 1995

[86] PCT No.: PCT/GB95/00324

§ 371 Date: Sep. 17, 1996

§ 102(e) Date: Sep. 17, 1996

[87] PCT Pub. No.: WO95/22254

PCT Pub. Date: Aug. 24, 1995

[30] Foreign Application Priority Data

Feb. 17, 1994 [EP] European Pat. Off. .............. 94301148

[51] Int. Cl.$^6$ .......................... A01N 65/00; A01N 59/16; A61K 35/78; A61K 33/26
[52] U.S. Cl. ................. 424/195.1; 424/404; 424/617; 424/647; 424/648
[58] Field of Search .................... 424/195.1, 648, 424/647, 617, 404

[56] References Cited

FOREIGN PATENT DOCUMENTS

| 1234397 | 10/1960 | France . |
| 53-029907 | 3/1978 | Japan . |
| 830064298 | 4/1984 | Japan . |
| 61-291892 | 6/1987 | Japan . |

OTHER PUBLICATIONS

Khaidarov et al. Chemical Abstracts, vol. 116 (26), Abstract No. 257791, 1992.
Azzouz et al. J. Food Prot., vol. 45 (14), pp. 1298–1301, 1982.

*Primary Examiner*—Leon B. Lankford, Jr.
*Assistant Examiner*—Christopher R. Tate
*Attorney, Agent, or Firm*—Wenderoth, Lind & Ponack, L.L.P.

[57] ABSTRACT

Antiviral and antifungal compositions comprising a mixture of a ferrous salt and a plant extract of pomegranate rind, *Viburnum plicatum* leaves or flowers, tea leaves, or maple leaves in an aqueous solution are disclosed. The compositions are mainly used to prevent the growth of, or kill, viruses or fungi on surfaces. The compositions do not substantially affect bacterial viability as measured by colony forming ability.

13 Claims, No Drawings

ANTIVIRAL OR ANTIFUNGAL COMPOSITION COMPRISING AN EXTRACT OF POMEGRANATE RIND OR OTHER PLANTS AND METHOD OF USE

Bacteriophage represent a diverse group of viruses that exert both positive and negative effects in microbiology. For example, in the dairy industry bacteriophages of the lactic acid bacteria represent a major source of starter culture failure with consequent poor-quality milk fermentations. A number of measures to prevent phage infection, including implementation of hygienic procedures, rotation of starter cultures, isolation of resistant mutants and formulation of media to suppress phage proliferation have been instituted with various degrees of success [1–4]. By contrast, coliphage have proven to be valuable monitors of faecal contamination in ground water and treated drinking water [5] and are effective viral models in studies of water quality and virucidal activity [6, 7]. Recent developments with genetically recombinant bacteriophage, containing either the bacterial luciferase lux genes or the ice nucleation gene ina, have established an additional value for phage in the rapid detection of bacteria in food and environmental samples [8–12]. In the above examples, the eventual destruction of bacteriophage is important either from the perspective of maintaining effective fermentation or from the viewpoint of good microbiological practice in the disposal of contaminated material. At present, the methods available for bacteriophage destruction such as heat and chemical disinfection [13, 14], have a significant impact on the viability and survival of associated bacteria. In the case of a sterilisation regime this is of little significance but the ability to combat bacteriophage in industrial environments would benefit from an environmentally benign procedure that could differentially destroy the virus without damaging metabolically-active bacterial cells. One example is in the dairy industry as mentioned above. Another concerns spraying plants which have symbiotic bacteria to control bacteriophage infection.

There are also many situations where it would be useful to be able to combat fungus without at the same time damaging metabolically-active cells. Plant extracts have been used against disease development in banana by fungi [15].

This invention provides an antiviral or antifungal composition comprising an effective concentration of a mixture of a ferrous salt and an extract of a plant selected from pomegranate rind, Viburnum plicatum leaves or flowers, tea leaves and maple leaves.

An antiviral composition is one which combats, e.g. by preventing growth or preferably killing, virus such as bacteriophage. An antifungal composition is one which combats, e.g. by preventing growth and preferably by killing fungus and destroying its spores. Preferred compositions are antiviral or antifungal, but without at the same time substantially damaging metabolically active bacterial or other cells with which the virus or fungus is associated. Preferably the composition is an aqueous solution, i.e. one in which water is the sole or the main constituent solvent.

The composition comprises a ferrous salt, which may conveniently be ferrous sulphate. The nature of the anion is however not critical, provided that the salt is non-toxic to bacterial and other cells under the intended conditions of use and is water-soluble. A preferred ferrous salt concentration range is 0.1 mM to 0.1M, particularly from 1 to 20 mM.

The composition also contains an extract of a plant. These plant extracts may conveniently be prepared by boiling the comminuted plant part with water or other solvent. The resulting extract may be fractionated. It is probable that the extract contains one or more active components. Although such active components have remained refractive to purification, there is a uniform consistency in the extracted activity from different sources of the plant parts and from parts obtained at different times of the year. The inventors have examined many different plants and have identified the following four as active:

Pomegranate rind. Whole pomegranates can be comminuted and used, but the activity resides in the rind.

Viburnum plicatum leaves or flowers.

Tea leaves. These may be dried or green. Other parts of the tea plant Camellia sinensis may be used.

Maple leaves e.g. UK Acer pseudoylatanus or Canadian maple leaves, or more generally leaves or flowers of any part of the genus Acer.

The plant extract may be used as is, or diluted as appropriate, e.g. by a factor of up to 100. Effective compositions generally contain 10–90% by volume of the ferrous salt solution together with correspondingly 90–10% by volume of the concentrated or diluted plant extract. The composition should preferably be stored in the dark.

The invention also includes solid or liquid concentrates which on dilution with water gives compositions as described.

The invention also includes a method of controlling virus or fungus, which method comprises contacting the virus or fungus with an effective concentration of a ferrous salt and an effective concentration of an extract of a plant selected from pomegranate rind, Viburnum plicatum leaves or flowers, tea leaves and maple leaves. These two components can be used in sequence in either order. Preferably, however they are used mixed together as a composition as described above.

The virus or fungus to be controlled may be contacted with, e.g. immersed in, the composition, typically for a few seconds or minutes. Where the virus or fungus is on a surface, the composition may be applied to the surface, e.g. by spraying or wiping.

The surface may be for example a work surface or a vessel or utensil used in a hospital or kitchen or an industrial environment, or an external surface of a mammal e.g. a human or a plant. Or a solution containing virus or fungus may be mixed with a composition as defined.

As described in the examples below, ferrous sulphate in combination with selected plant extracts effects complete destruction of a broad range of bacteriophage infecting diverse bacterial genera. In assays incorporating both bacteriophage and bacteria at $10^{12}$ and $10^9$/ml respectively, the bacteriophage are entirely destroyed within two minutes without affecting bacterial viability as measured by colony forming ability.

When used alone, ferrous sulphate has virucidal activity against phages, and also bactericidal activity against some bacteria. This invention is based on the observation that ferrous sulphate, either alone or in combination with certain plant extracts, offers a potent broad spectrum virucidal activity. Since the activity of relatively low levels of ferrous sulphate can be further potentiated by the addition of trace amounts of hydrogen peroxide (data not shown) it is likely that the mechanism of action involves, at least in part, a free radical system. A mechanism similar to that operating in the phagolysozome and defined by the Modified Haber-Weiss Reaction [17] is proposed.

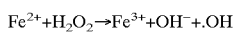

$$Fe^{2+}+H_2O_2 \rightarrow Fe^{3+}+OH^-+\cdot OH$$

While resistance of bacterial cells may be effected through free radical scavenging and repair systems, it is clear that the plant extracts also have a role and that remains to be elucidated.

Materials and Method

Bacteria and bacteriophage strains

One Gram-positive *Staphylococcus aureus* NCIMB 8588 and two Gram-negative *Salmonella typhimurium* LT2 and *Pseudomonas aeruginosa* NCIMB 10548 bacteria were used. The bacteriophage with specificity for the above bacteria were NCIMB 9563 for *Staph.aureus*, Felix 01 for *S.typhimurium* [16](obtained from Amersham International plc., Amersham, HP7 9NA, UK) and NCIMB 10116 and 10884 for *Ps.aeruainosa*. (All these bacteria and bacteriophage are available to the public.)

The bacterial cells were maintained on Tryptose Phosphate Broth (TPB; Oxoid) supplemented with 1% agar (TPA) and stored at 4° C. with monthly subculture. When required, cells were resuscitated in 10 ml TPB (18h, 37° C.) or an orbital shaker operating at 240 rpm. Appropriate bacterial dilutions were made in Lambda buffer (6 mM Tris, 10 mM $MgSO_4.7H_2O$, 50 µg/ml gelatin; pH 7.2). After treatment bacterial survival was determined by colony forming units (cfu) on TPA [18].

Phage stocks were developed on their appropriate host strains by a plate lysis procedure essentially equivalent to growing bacteriophage Lambda-derived vectors [19]. Typical phage titres of $10^{12}$/ml were obtained. Phage stocks were maintained in Lambda buffer at 4° C. and stocks retained a constant titre for several months.

Preparation of plant extracts

Pomegranate rind, *Viburnum plicatum* leaves or flowers, maple leaves and commercial tea leaves were blended in distilled water (25% w/v) and boiled for 10 min. After centrifugation (20,000 ×g, 4° C., 30 min), supernatants were autoclaved (121° C., 15 min), cooled and stored at −20° C. A further purification of the pomegranate extract to a molecular weight cut-off of 10,000 Da was achieved by membrane ultra filtration and the filtrate stored as above.

EXAMPLE 1

Preparation of Composition A a. Preparation of 4.3 mM $FeSO_4.7H_2O$ in Lambda-buffer First freshly prepare stock solution (0.53%) of $FeSO_4.7H_2O$ (0.053 gm ferrous sulphate in 10 ml Lambda-buffer). After sterilisation by membrane filtration (0.45 µm, Whatman) prepare the final ferrous sulphate concentration of 4.3 mM by transferring 4.1 ml of the ferrous stock solution to a sterile test tube containing 14 ml of Lambda-buffer.

b. Preparation of 13% PRE (pomegranate rind extract)

Mix 1.3 ml of stock solution of PRE (25% w/v) with 8.7 ml of Lambda-buffer.

Composition A was prepared 1–2 min prior to use by mixing 16.74 ml of 4.3 mM $FeSO_4.7H_2O$ (a; yellow) with 8.265 ml of 13% PRE (b; yellow). After about 30 sec the colour of the mixture (a and b) changed greenish then to black. These mixtures of ferrous sulphate and PRE (a and b) should be protected from light.

EXAMPLE 2

Virucidal Assay

Plant extracts were diluted 1:8 in Lambda buffer immediately prior to use and 300 µl of this diluted extract added to 700 µl of freshly prepared ferrous sulphate solution (4.3 mM $FeSO_4.7H_2O$; pH 6.5); these mixtures should be protected from light. Bacteriophage (20 µl at $10^{12}$ pfu/ml) or 20 µl of an appropriate dilution of bacteria ($10^9$ cfu/ml) were placed in a sterile Eppendorf micro-centrifuge tube and 144 µl of the $FeSO_4$ solution or PRE solution or composition A (Example 1) or of the above plant extract/$FeSO_4$ mixture added. After exposure of the bacteriophage or bacteria for 2 min at room temperature the activity of the mixture was neutralised by adding an equal volume of 2t (v/v) Tween 80 in Lambda buffer. The number of bacteriophage or bacteria surviving the above protocol were measured by plaque forming units (pfu) or colony forming units respectively.

The results are set out in the following Tables 1 and 2. Table 1 indicates that pomegranate rind extract alone has a slight virucidal activity against Pseudomonas phage but in combination with $FeSO_4$ there is a profound synergy. Eleven log reductions in plaque forming ability are obtained within 2 min. A similar synergy of virucidal action was achieved with other plant extracts, leaves and flowers of *Viburnum plicatum*, maple leaves and tea leaves (Table 2).

Our particular interest in the above studies was to select agents with maximal virucidal activity whilst having little effect on bacteria. In this regard $FeSO_4$, either alone or in combination with pomegranate rind extract, appears singularly successful. Table 1 shows that for each bacterium and phage combination tested there is a simple treatment that can eliminate bacteriophage activity without affecting bacterial visibility. The plant extracts appear to serve a dual role in their interaction with $FeSO_4$. In the case of Pseudomonas phage they promote virucidal activity while for the Salmonella phage, which is completely inactivated by $FeSO_4$ alone, the pomegranate rind extract appears to provide a significant protection to the bacterium.

TABLE 1

The survival of different bacteria and bacteriophage species in 4.3 mM $FeSO_4.7 H_2O$, 13% PRE (pomegranate rind extract; 20 min at 37° C.) and Composition A (PRE + 4.3 mM $FeSO_4.7 H_2O$; 2 min at room temperature) prepared in Lambda buffer.

| Microorganisms | Lambda Buffer | 13% PRE | 4.3 mM $FeSO_4.7 H_2O$ | Composition A* |
|---|---|---|---|---|
| *Bacteriophage species* (pfu/ml): | | | | |
| *Staphylococcus* NCIMB 9563 | $7 \times 10^{11}$ | $2 \times 10^7$ | Nil | Nil |
| *Salmonella* Felix 01 | $3 \times 10^{12}$ | $3 \times 10^{12}$ | Nil | Nil |
| *Pseudamonas* NCIMB 10884 | $5 \times 10^{11}$ | $5 \times 10^9$ | $5 \times 10^{11}$ | Nil |
| *Pseudamonas* NCIMB 10116 | $5 \times 10^{11}$ | $5 \times 10^8$ | $5 \times 10^{11}$ | Nil |
| Bacteria species (cfu/ml): | | | | |
| *Staph.aureus* NCIMB 8588 | $3 \times 10^9$ | $2 \times 10^6$ | $3 \times 10^9$ | $5 \times 10^6$ |

TABLE 1-continued

The survival of different bacteria and
bacteriophage species in 4.3 mM FeSO$_4$.7 H$_2$O, 13% PRE
(pomegranate rind extract; 20 min at 37° C.) and
Composition A (PRE + 4.3 mM FeSO$_4$.7 H$_2$O; 2 min at room
temperature) prepared in Lambda buffer.

| Microorganisms | Lambda Buffer | 13% PRE | 4.3 mM FeSO$_4$.7 H$_2$O | Composition A* |
|---|---|---|---|---|
| S.typhimurium LT2 | $2 \times 10^9$ | $2 \times 10^9$ | Nil | $2 \times 10^9$ |
| Ps.aeruginosa NCIMB 10548 | $4 \times 10^9$ | $4 \times 10^9$ | $1 \times 10^7$ | $4 \times 10^9$ |

*Escherichia coli phage M13mp18 was killed by Composition A, whilst E. coli JM101 was unaffected.

TABLE 2

Effect of 25% solutions of different plant
extracts in the presence of 4.3 mMol ferrous sulphate
on the inactivation within 3 minutes of Ps.aeruginosa
bacteriophage NCIMB 10116.

| 25% Plant extract solution (% v/v) | PFU/ml |
|---|---|
| Lambda Buffer (control) | $1.2 \times 10^{10}$ |
| Commercial tea leaves | Nil |
| Viburnum plicatum leaves or flowers | Nil |
| Maple leaves | Nil |

An antiserum was raised in rabbits against the Pseudomonas phage. A classic precipitin band was obtained with a double-immunodiffusion assay of phage antigen against this antiserum. No such precipitin band was obtained, however, when the phage had been treated with the virucidal agent, nor if the antiserum had been raised against treated phage.

Treated phage were further examined by electron microscopy. No recognisable phage morphological structures remained in any of the twenty fields examined. The result of the further tests are consistent, therefore, with a complete destruction of the bacteriophage structure by the virucidal composition, to an extent that antigenic determinants are lost.

EXAMPLE 3
Antifungal Test

Apple leaves infected with powdery mildew were immersed in Composition A (Example 1) for about 60 seconds or until the leaves were completely wetted. The leaves were then observed daily. The powdery mildew was completely inhibited within 24 hours and no mildew lesions were present on the treated apple leaves as they hardened off.

A further microscopic test of treated powdery mildew spores and mycellium with Composition A showed that both spores and mycellium were destroyed after 1 hour at room temperature. Composition A neutralised by 2%. TW80 was not effective however.

EXAMPLE 4

Composition A was tested under the conditions described in Example 2 for activity against poliovirus, herpes simplex virus type 1. (HSV-1) and human immunodeficiency virus type 1. 20 µl of an appropriate dilution of virus was mixed with 144 µl of composition A. After exposure, the virucide was neutralised by addition of a 2% v/v solution of Tween 80 in lambda buffer. In cell culture assays using HT-29 cells (for poliovirus), MRC-5 cells for HSV-1 and HUT-78 cells for HIV-1 there was complete reduction of infectivity of initial inocula of 1–4 ×10$^6$ virus. There was no apparent cytopathic effect on MRC-5 cells or HT-29 cells.

REFERENCES

1. Terzaghi, B. E. and Sandine,, W. E. (1975) Improved medium for lactic streptocci and their bacteriophages. Appl. Microbiol. 29, 807–813.
2. Marshall, R. J. and Berridge, N. J. (1976) Selection and some properties of phage-resistant starter for cheese-making. J. Dairy Res. 43, 449–458.
3. Thunell, R., Sandine, W. E. and Bodyfelt, F. (1981) Phage insensitive, multiple-strain starter approach to cheddar cheese. J. Dairy Sci. 64, 2270–2277.
4. Sing. W. D. and Klaenhammer, T. R. (1993) A strategy for rotation of different bacteriophage defenses in a lactococcal single-strain starter culture system. Appl. Environ. Microbiol. 59, 365–372.
5. Dutka, B. J., Palmateer, G. A., Meissner, S. M., Janzen, E. M. and Sakellaris, M. (1990) The presence of bacterial virus in groundwater and treated drinking water. Environ. Pollut. 63, 293–298.
6. Jassim, S. A. A., Ellison, A., Denyer, S. P. and Stewart, G. S. A. B. (1990). In vivo bioluminescence: a cellular reporter fo research and industry. J. Biolumin. Chemilumin. 5, 115–122.
7. Mesquita, M. M. F. D. (1990) Bacteriophages as viral models in studies of water and shellfish quality. Rev. Bras. Biol. 49, 923–932.
8. Ulitzur, S. and Kuhn, J. (1987) Introduction of lux genes into bacteria, a new approach for specific determination of bacteria and their antibiotic susceptibility. In Bioluminescence and Chemiluminescence New Perspectives, (Schlomerich, J., Andereesen, R., Kapp, A., Ernst, M. and Woods, W. G. Eds), pp. 463–472. Bristol:Wiley.
9. Stewart, G. S. A. B., Smith, A. T. and Denyer, S. P. (1989) Genetic engineering of bioluminescent bacteria. Food Sci. Technol. Today. 3, 19–22.
10. Wolber, P. K. and Green, R. L. (1990) New rapid method for the detection of Salmonella in foods. Trends Food Sci. Technol. 1, 80–82.
11. Kodikara, C. P., Crew, H. H. and Stewart, G. S. A. B. (1991) Near on-line detection of enteric bacteria using lux recombinanat bacteriophage, FEMS Microbiol. Letts. 83, 261–266.
12. Turpin, P. E., Maycroft, K. A., Bedford, J., Rowlands, C. L. and Wellington, E. M. H. (1993) A rapid luminescent-phage based MPN metahod for the enumeration of Salmonella typhimurium in environmental samples. Letts. Appl. Microbiol. 16, 24–27.
13. Adams, M. H. (1959) Bacteriophages, 49–62 pp. Wiley Interscience.
14. Maillard et al. (1993) Effect of biocides on Pseudomonas aeruginosa phage F116. Letts. Appl. Microbiol. 17, 167–170.
15. Singh, et al. (1993) Letts. Appl. Microbiol. 17, 269–271.

16. Kallings, L. O. (1967) Sensitivity of various Salmonella strains to Felix 01 phage. Acta Pathol. Microbiol. Scand. 70, 446–454.
17. Fantone, J. C. and Ward, P. A. (1982) Role of oxygen-derived free radicals and metabolites in leukocyte-dependent inflammatory reactions. Am. J. Pathol. 107, 397–418.
18. Miles, A. A., Misra, S. S. and Irwin, J. O. (1938) The estimation of the bactericidal power of the blood. J. Hyg. (Cambridge), 38, 732–749.
19. Ausubel, F. M., Brent, R., Kingston, R. E., Moore, D. D., Seidman, J. G., Smith, J. A. and Struhl, K. (1991) Growing lambda-derived vectors In Current Protocols in Molecular Biology, Vol. 1, pp 1.12.1–1.12.3., Wiley Interscience, New York.

We claim:

1. An antiviral or antifungal composition for treating surfaces, comprising an effective concentration of a mixture of a ferrous salt and an extract of pomegranate rind, wherein said composition does not substantially affect bacterial viability as measured by colony forming ability.

2. The composition as claimed in claim 1, which is an aqueous solution.

3. The composition as claimed in claim 2, wherein the ferrous salt concentration is 0.1 mM to 0.1M.

4. The composition as claimed in claim 2 or 3, wherein the pomegranate rind extract is used at a dilution of 1 to 100 times.

5. The composition as claimed in claim 2 or 3, wherein the ferrous salt is ferrous sulphate used at a concentration of 1–20 mM.

6. A solid or liquid concentrate which on dilution with water gives a composition according to claim 2 or 3.

7. A method of preventing growth of, or killing, viruses or fungi on a surface, which method comprises contacting the virus or fungus with a composition comprising an effective concentration of a mixture of a ferrous salt and an extract of pomegranate rind, wherein said composition does not substantially affect bacterial viability as measured by colony forming ability.

8. The method as claimed in claim 7, wherein the ferrous salt is used as a 0.1 mM to 0.1M aqueous solution.

9. The composition as claimed in claim 4, wherein the ferrous salt is ferrous sulphate used at a concentration of 1–20 mM.

10. A solid or liquid concentrate which on dilution with water gives a composition according to claim 4.

11. A solid or liquid concentrate which on dilution with water gives a composition according to claim 5.

12. A solid or liquid concentrate which on dilution with water gives a composition according to claim 9.

13. The method as claimed in claim 7 wherein the virus or fungus is contacted with an aqueous composition comprising a mixture of the ferrous salt and the plant pomegranate rind extract.

* * * * *